United States Patent [19]

Bayer et al.

[11] Patent Number: 4,956,181

[45] Date of Patent: Sep. 11, 1990

[54] NITRATE THERAPY FOR ANGINA PECTORIS

[75] Inventors: Gerald W. Bayer; Paul A. Diamantopoulos, both of Rochester; Hans W. Osterhoudt, Spencerport; Paul F. Schmit, Rochester, all of N.Y.

[73] Assignee: Eastman Kodak, Rochester, N.Y.

[21] Appl. No.: 203,774

[22] Filed: Jun. 7, 1988

Related U.S. Application Data

[63] Continuation of Ser. No. 47,954, May 8, 1987, abandoned.

[51] Int. Cl.$^5$ ............................................. A61F 13/40
[52] U.S. Cl. ..................................... 424/448; 424/447
[58] Field of Search ................................ 424/448, 449

[56] References Cited

U.S. PATENT DOCUMENTS

| | | | |
|---|---|---|---|
| 4,117,841 | 10/1978 | Perrotta et al. | 424/448 |
| 4,725,272 | 2/1988 | Gale | 424/449 |
| 4,752,478 | 6/1988 | Bondi et al. | 424/449 |

OTHER PUBLICATIONS

Ho-Leung Fung, Ph.D., "Pharmacokinetic Determinants of Nitrate Action," The American Journal of Medicine, 6/22/84, pp. 22–26.

Steven Corwin, MD, James A. Reiffel, MD, "Nitrate Therapy for Angina Pectoris," *Arch. Intern. Med.*, vol. 145, Mar., 1985, pp. 538–543.

Johathan Abrams, MD, "Pharmacology of Nitroglycerine and Long-Acting Nitrates," *Am. J. Cardiol.*, 1985, vol. 56, pp. 12A–18A.

John O. Parker, MD, "Nitrate Tolerance," *Am J. Cardiol.*, 1985, vol. 56, pp. 281–311.

John T. Flaherty, MD, "Hemodynamic Attenuation and the Nitrate-Free Interval: Alternative Dosing Strataegies for Transdermal Nitroglycerine," *Am. J. Cardiol*, vol. 56, pp. 321–371.

*Primary Examiner*—Thurman K. Page
*Assistant Examiner*—Leon R. Horne

[57] ABSTRACT

Method and device for treating angina pectoris and preventing tolerance to nitrate drugs which takes into account the frequent need to provide the patient with relief from or prevention of pre-waking or early morning angina. The treatment comprises administering a daily unit dose of the nitrate before bedtime in a dosage form that (1) provides a washout period of 3 to 12 hours by sufficiently retarding delivery of the nitrate to the patient during the washout period so as to provide a rate of delivery of nitrate from the patch that is so low as to be insufficient to cause tolerance to said nitrate in said patient; (2) at the end of the washout period and at least 30 minutes before the patient expects to awaken, initiates an effective delivery period during which the dosage form provides an initial effective delivery rate sufficient to provide an antianginally effective concentration of nitrate in the blood stream of the patient; and (3) thereafter, during a ramp-up delivery period, delivers the nitrate at an increasing rate until a final delivery rate is achieved, which is from 125% to 1,000% of the initial effective delivery rate. At the end of the ramp-up period, delivery is exhausted or otherwise terminated. A new unit dose is administered at bedtime, and the cycle is repeated. A preferred transdermal patch for carrying out the treatment is provided.

27 Claims, 5 Drawing Sheets

NITRATE THERAPY FOR ANGINA PECTORIS

This is a continuation of application Ser. No. 047,954, filed May 8, 1987, now abandoned.

FIELD OF THE INVENTION

The present invention relates to the treatment of patients having angina pectoris, particularly the form known as chronic, stable angina pectoris.

DESCRIPTION RELATIVE TO THE PRIOR ART

Nitroglycerine (also commonly referred to as trinitroglycerine or glycerine trinitrate, and often referred to hereinafter by its common abbreviation, (TNG) has been used to treat angina pectoris for over 100 years. Nitroglycerine (TNG) and other organic nitrates have been available for the treatment of angina and congestive heart failure in a number of different dosage forms for some time. These include sublingual, oral and buccal tablets as well as capsules, topical creams and ointments, patches, tapes, inhalable sprays and intravenous solutions. Transdermal nitroglycerine patches were introduced in recent years in an effort to overcome some of the disadvantages and inconveniences of other dosage forms. In particular, they were formulated to provide increased systemic bioavailability as well as constant delivery of the drug over a 24 hour period or longer. They have become popular in the treatment of chronic, stable angina. Typically, the patches are applied once daily, either in the morning or evening, and changed daily at approximately the same time.

Recently, the results of a number of clinical studies have raised questions regarding the efficacy of chronic nitrate therapy due to the observed development of tolerance or hemodynamic attenuation during long term nitrate therapy in general and, in particular, nitrate therapy using transdermal patches. This phenomenon, among others, has been discussed, for example, in the following representative articles in the medical literature:

(1) "Pharmacokinetic Determinants of Nitrate Action", Ho-Leung Fung, Ph.D., *The American Journal of Medicine*, June 22, 1984, pages 22-26. The author states that the issue of nitrate tolerance in the clinical setting is controversial. He further speculates that the actual systemic concentration, as such, may be less important than the change in concentration with time in producing beneficial effects from nitrates, and that "the rate of drug input may yet be another determinant of nitrate action." He postulates that an alternate input mode, particularly for transdermal nitroglycerin, "might be one that involves escalating rates of drug delivery so that increasing systemic nitrate concentrations may be achieved. If nitrate tolerance is a concern over the 24-hour dosing period, then a drug washout period may be incorporated (most likely during the sleeping hours) . . . " He concludes that "the validity of this dosing approach has to be experimentally tested, and the potential problems arising from it (for example, control of nocturnal angina) are yet to be fully appreciated."

(2) "Nitrate Therapy for Angina Pectoris", Steven Corwin, MD, James A. Reiffel, MD, *Arch Intern. Med.*, Vol. 145, Mar. 1985, pages 538-543. After reviewing the efficacy and mechanism of action of various nitrate preparations, the authors state that it is a matter of debate whether tolerance develops in patients receiving nitrates over long time periods, but suggest that the clinician should be aware of this possibility when using these agents.

(3) "Pharmacology of Nitroglycerine and Long-Acting Nitrates", Jonathan Abrams, MD, *Am J Cardiol*, 1985, vol. 56, pages 12A-18A. Dr. Abrams concludes his article with a discussion of nitrate tolerance in which he indicates that this remains "a vexing and difficult problem." He notes that there have been suggestions that providing sustained nitrate plasma concentrations or repeated administration of large doses may induce tolerance more readily than interrupted or lower dose therapy, and that this may be particularly relevant to transdermal nitroglycerine. He suggests that the clinician be prepared to change the nitrate dosage regimen when it appears that there may be tolerance—either discontinuing nitrates for "a short period of time or increas[ing] the dose, or both."

(4) "Nitrate Tolerance", John O. Parker, MD, *Am J Cardiol*, 1985, Vol. 56, pages 281-311. Dr. Parker reports the results of studies using both oral and transdermal isosorbide dinitrate and transdermal nitroglycerine as indicating that tolerance developed with long term administration in each case. However, short washout periods of as little as 9 hours between oral doses or transdermal patch applications seemed to avoid the tolerance effect in angina patients. He concludes that "it appears desirable to prescribe oral nitrates on a 3-times-a-day basis, with no medication after the supper dose. With transdermal preparations, one could postulate that it would be best to remove the patches after 12 or 16 hours of application to allow overnight washout."

(5) "Hemodynamic Attenuation and the Nitrate-Free Interval: Alternative Dosing Strategies for Transdermal Nitroglycerine", John T. Flaherty, MD, *Am J Cardiol*, 1985, vol. 56, pages 321-371. This author also finds that his review of the data of other investigators suggests that clinically significant tolerance occurs with all forms of long-term nitrate therapy when administered continuously. He is uncertain whether higher doses administered continuously can overcome this effect, and asserts both that further testing is required, and that it seems equally likely that a nitrate-free interval, e.g., by interrupting administration during the night, might provide a means for avoiding tolerance. This could be accomplished, he suggests, by removing the patch at night and applying a new one in the morning, or, in the case of oral, buccal or ointment preparations, omitting the last otherwise administered dose at the end of the day. This author also stresses the importance of dose titration in individual patients.

It is worth noting that nowhere in the literature of which we are aware have there been any reports of the results of actual testing of the effects on tolerance of a long term therapy involving overnight drug-free washout periods followed by delivery of the nitrate at a steadily increasing rate during the day. Moreover, none of the above postulated solutions for nitrate tolerance provides guidance with respect to delivery rates, rates of increase of delivery, or levels to which delivery should be increased in order to provide effective therapy as well as avoid both tolerance and unwanted side effects. In addition, we are unaware of any proposal or suggestion for such a method which takes into account the frequent need to provide the angina patient with relief from or prevention of pre-waking or early morning angina.

Thus, as is well known to those skilled in the art of treating angina, many angina patients chronically experience discomfort during sleep, just before awakening and for the first hour or so upon awakening. While tolerance to nitrates also has been found to be a problem for many angina patients, the solutions heretofore proposed for tolerance of which we are aware do not seem to have both proposed a washout period and provided for administering to the patient an antianginally effective amount of nitrate during the prewaking period.

SUMMARY OF THE INVENTION

We have now discovered that nitrate tolerance can be avoided while providing effective treatment to angina patients, particularly chronic, stable angina pectoris patients, including providing protection from angina attacks in the critical pre-waking and early morning period upon and shortly after arising from sleep, by a dosage administration regimen which comprises the steps of (1) administering to a patient in need thereof a premeasured amount (daily unit dosage) of an organic nitrate that is effective to treat angina in a dosage form that includes means for retarding delivery of said nitrate from said dosage form to said patient for a washout period of from about 3 to about 12 hours to provide a rate of delivery of nitrate during said washout period in the range between none and a delivery rate so low as to not cause tolerance to said nitrate in said patient, said delivery rate preferably being substantially nil during at least most of said washout period; (2) causing a rise in delivery of the nitrate to an initial effective delivery rate, i.e. a delivery rate which provides an antianginally effective level of the nitrate in the patient's blood stream, at least about 30 minutes, and up to about two hours, before arising; (3) thereafter, within at least about four hours of achieving the effective delivery rate, increasing the delivery rate to a final rate of from about 125% to about 1,000%, preferably from about 125% to about 600%, more preferably from about 150% to about 400%, of the initial effective rate over a ramp-up delivery period of from about 8 to about 21 hours, preferably from about 12 to about 18 hours; (4) causing delivery of said nitrate from said first dosage unit to terminate at the end of said ramp-up period; and (5) administering a new dosage unit to start a new administration cycle at step (1). In this manner, effective, long-term treatment of angina pectoris is provided while avoiding both between day and within day tolerance effects and at the same time providing effective protection in the often critical period before, at, and soon after waking, as well as through the periods of the day when most angina attacks occur.

The invention also provides means for carrying out the foregoing dosage regimen. Broadly, this aspect of the invention comprises a drug delivery device for avoiding tolerance to an organic nitrate drug comprising;

a. organic nitrate drug containing means comprising a unit dose of said nitrate in a dosage form capable of delivering said nitrate to the blood stream of a patient in need thereof, said unit dose being of a sufficient amount to provide effective nitrate therapy for at least about a day;

b. means for bringing said device into drug delivery relationship with said patient;

c. means for sufficiently retarding delivery of said nitrate from said containing means to said patient for a predetermined washout period after said device is brought into said drug delivery relationship that the rate of delivery of nitrate during said washout period is in the range between none and a delivery rate so low as to be insufficient to cause tolerance to said nitrate in said patient;

d. means for initiating delivery of said drug to said blood stream at the end of said washout period so as to achieve an initial effective delivery rate at least about 30 minutes before the patient expects to awaken;

e. means for initiating a ramp up period within about 4 hours after achieving said initial effective drug delivery rate, during which ramp up period said drug is delivered at an increasing rate until a final drug delivery rate of from about 125% to about 1,000% of said initial effective rate is achieved, said initiating means comprising means for effecting said increasing rate and for maintaining said increasing rate for a ramp up period of from about 8 to about 21 hours; and f. means for causing substantial termination of delivery of said drug at the end of said ramp up period.

The above-described device in accordance with the present invention can take virtually as many different forms as there are dosage forms available for delivery of nitrate drugs to patients, so long as such dosage forms contain, or are associated with, cooperating means for carrying out the functions delineated above. It should also be understood that the same physical element can comprise more than one of the above-defined means, and that, conversely, a multiplicity of different elements may be combined to constitute a single one of the foregoing means. While many such devices can be made within the spirit and scope of the present invention, the invention will be described hereafter, particularly in the detailed descriptions of the invention, primarily with respect to a presently preferred delivery device, namely, a transdermal patch.

In connection with the foregoing, transdermal drug delivery devices in accordance with this invention can comprise certain components of conventional drug delivery patches, for example, a conventional release liner on the bottom of the element for protection and containment of the drug composition; a known pressure-sensitive adhesive serving to retain and subsequently allow easy removal of the release liner, and then allow application of the element to the skin of the patient by applying hand pressure; a carrier for the drug composition such as lactose, porous silica gel beads, porous glass beads, porous polymer beads, and other such carriers that can sorb the drug internally or on their surfaces; and, of course, protective frontal and backing layers, and packages, for example, pouch enclosures made from polymer/metal foil laminates.

In addition to conventional components, the elements of this invention necessarily additionally comprise a means for delaying the onset of delivery of the drug for a predetermined washout period, means for initiating rapid drug delivery after the washout period, and means for providing a continuing ramp-up delivery period during which the drug is delivered to the patient at a gradually increasing rate. Means for causing substantial termination of the drug delivery at the end of the ramp-up period can be provided either by so loading the transdermal device that substantial depletion of the drug composition occurs at the end of the ramp-up period or by providing means for removing the device at that time, e.g. by peeling a transdermal patch from the skin, etc.

DETAILED DESCRIPTION OF THE INVENTION

In general, the drug-containing means of a transdermal patch in accordance with the invention will comprise a reservoir for the drug composition that is impermeable to the components of the drug composition, at least until time for application of the device. The reservoir can be a separate container within or appended to the device, such as a rupturable pod from which the drug composition can be delivered to the interior of the delivery device upon breaking the pod. Alternatively, the reservoir can be formed by separate drug composition-impermeable layers which allow drug transport only upon activation such as by one or more of: physical stimulation, heating, pH adjustment, electrical stimulation, and the like.

The drug composition contained within the pod or other drug containing means generally comprises (1) the nitrate drug to be delivered, such as trinitroglycerine, isosorbide mononitrate, isosorbide dinitrate, erythrityl tetranitrate, pentaerythritol tetranitrate, and other effective antianginal organic nitrate compositions; (2) a carrier for the drug such as lactose or a porous bead composition, e.g., porous glass beads, porous polymer beads, silica gel or the like; (3) a solvent such as water, an aliphatic alcohol, dimethyl sulfoxide, or the like, and in a presently preferred embodiment, includes at least one activator chemical which serves to alter the properties of the barrier layer described hereinafter, e.g. by plasticizing the polymer, so as to increase the permeability of the nitrate therethrough. The same or another activator chemical may optionally serve to promote absorption of the nitrate by the skin.

The means for bringing the device into drug delivery relationship with the patient, in a patch of the present invention, generally will comprise a pressure-sensitive adhesive which preferably is the entire, uniform layer that contacts the skin and does not act to limit the rate of diffusion of drug from the patch to the skin. Alternatively, the adhesive can be a peripheral boundary on the underside of the patch. In either event, the adhesive is covered by a conventional release liner which is removed by peeling when the patch is to be applied to the skin.

Means for retarding delivery of said nitrate from a patch of the present invention to the patient conveniently comprises at least one barrier layer separating the drug composition from the side of the device that is applied to the patient. As indicated above, the barrier layer can be employed in combination with an activator agent (generally contained in the drug composition) that will attack and render the barrier layer permeable to the drug after an activation period corresponding essentially with the desired delay period. Preferred barrier layers are drug-impermeable polymer layers that can be attacked by an activator such as an organic plasticizer, or solvent, or a pH controlled aqueous solution. Useful barrier polymers include rubbery vinyl copolymers such as poly(ethylene-co-vinyl acetate) polymers comprising up to about 10% by weight vinyl acetate repeating units (EVA resins); copolymers of styrene with ethylene and butylene or with butadiene such as those sold under the trade name Kraton by Shell Chemical Co.; styrene-butadiene and styrene-isoprene copolymers such as those sold under the trade name Solprene by Phillips Petroleum Co. and under the trade name Stereon 881A by Firestone; polymers of vinyl ethers such as poly(vinyl isobutyl ether); polymers of vinyl chloride, polymers of vinyl acetate; and acrylic and acrylamide polymers prepared as bulk, solution, or latex polymers that can be sufficiently coalesced upon coating to produce the required drug-impermeability. Also useful as barrier layers are polymers of ethylene, propylene, isoprene, butadiene, alkyl acrylates, alkyl methacrylates, acrylamides, methacrylamides, acrylic acids, itaconic acid, crosslinking monomers such as divinylbenzene, ethylene diacrylate, N,N'-methylenebisacrylamide and ethylene dimethacrylate, crosslinkable monomers such as hydroxyl monomers e.g., hydroxyethyl methacrylate, active methylene monomers, e.g., 2-acetoacetoxyethyl methacrylate, amines such as 2-aminoethyl methacrylate hydrochloride, and ionic monomers including the aforementioned carboxylic acids and salts thereof as well as sulfonic acids and their salts such as sodium 2-acrylamido-2-methylpropanesulfonate, cellulose esters such as cellulose acetate butyrate, and low molecular weight polyethers such as ethylene oxide and propylene oxide homo- and copolymers. Of course, the polymers can be employed as mixtures in the barrier layers, and the layers can be combined to form double- or triple-layer barrier systems.

The activators for the barrier layers are preferably organic liquids such as alcohols, e.g., ethanol, propanol, isopropanol, isobutanol, hexanol, octanol, decanol, dodecanol, ethylene glycol, propylene glycol (1,2-propanediol), 1,3-propanediol, and glycerin; esters such as ethyl acetate, isopropyl myristate, lauryl myristate, decyl propionate, bis(2-ethylhexyl) phthalate, benzyl butyl phthalate, bis(2-ethylhexyl) sebacate, diisobutyl sebacate, di-n-butyl sebacate and diisopropyl adipate; and oils such as mineral oil; and other materials known to slowly soften, dissolve, and/or degrade the polymer barrier layer compositions with which they are used. The following listing includes additional materials that can be used as activators in the patches of the present invention: bis(n-octyl) phthalate, cetyl alcohol, dibutyl phthalate, diethyl sebacate, ethyl lactate, ethyl phthalate, glycerol monostearate, glycerol distearate, glycerol tristearate, isopropyl palmitate, isopropyl stearate, N,N-bis(2-hydroxyethyl)dodecanamide, lauric myristic monoethanolamide, lauryl lactate, myristyl alcohol, n-decyl methyl sulfoxide, N,N-dimethylacetamide, oleyl alcohol, phenylethyl alcohol, sodium lauryl sulfate, sodium stearate, stearyl alcohol, wood alcohols, 1,2,6-hexanetriol, water and 2-amino-2-methyl-1-propanol.

The activators are conveniently included in the drug composition and the entire drug composition isolated from the barrier layer(s) until the device is applied to the patient. This can be accomplished by containment of the drug-activator composition within a rupturable pod as described heretofore. In an alternative embodiment of the invention, the activator chemicals can be contained in another part of the transdermal delivery device, remote from the drug composition, for example, in a separate rupturable pod. In any event, the activator chemical(s) employed should be compatible with the nitrate drug and so contained in the device as to be capable of being brought into contact with the barrier polymer layer upon the occurrence of a selected event.

Means for initiating delivery of drug after the washout period can comprise, for example, one or a combination of:

(1) the plasticized, dissolved, or degraded barrier layer which, after having been acted upon by the appropriate activator, is adapted to allow drug diffusion to the skin of the patient after the washout period, and (2) skin softening, wetting, and/or absorption promoting agents that can be contained anywhere within the drug delivery device, i.e., on either side of the barrier layer(s). Such agents are conveniently a part of the drug composition and are thus contained isolated from the barrier layers. In certain preferred embodiments, the same material(s) serve(s) as both the barrier layer activator, e.g., plasticizer, and skin-absorption promoting agent. For example, when the barrier layer is poly(vinyl isobutyl ether), higher alcohols, such as octanol and decanol, function as both plasticizers for the barrier layer polymer and as skin-absorption promoters. Other skin absorption promoters known in the art can also be employed to facilitate initial rapid drug delivery through the skin.

A preferred means for initiating the ramp-up period comprises essentially the same combination of elements as described above in connection with the means for initiating drug delivery, these elements being so disposed that at a later time in the sequence they serve to cause the desired ramp-up delivery. Thus, as the concentration of the skin absorption promoter increases at, and through, the surface of the skin, the flux of drug delivery through the skin and into the patient's bloodstream also increases. Other techniques, including heat and ultrasonic energy could also be employed to control the rate of drug delivery to or through the skin.

Means for causing substantial termination of delivery of the drug may be inherent in the amount of the drug incorporated in the patch but more conveniently comprises the entire patch, which can be removed conveniently by peeling from the patient's skin. Termination of drug delivery can also be facilitated by depletion of the skin absorption promoter or by means for reversing the drug permeability of the barrier polymer layer.

Figure 1:
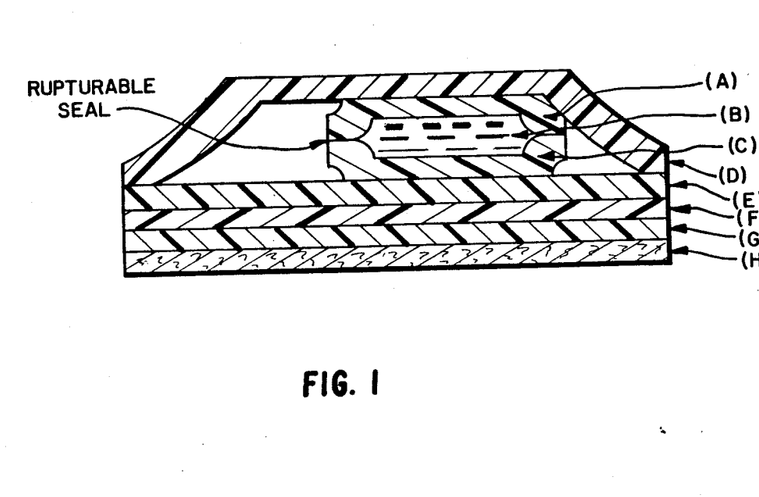
FIG. 1 is a schematic drawing, in section, of a transdermal patch of the present invention.

A presently preferred transdermal patch in accordance with the present invention is illustrated in the schematic drawing of FIG. 1 and comprises, in combination:

(i) an occlusive backing layer (D) comprising a laminate of an occlusive polymeric film [preferably a polyester film such as poly(ethylene terephthalate)] laminated to a heat-sealable film such as polyolefin film, for example polyethylene, or polypropylene and, optionally, an additional (outer) layer comprising aluminum or an aluminized film covering or laminated to the opposite face of the occlusive film.

(ii) a pod reservoir for containing an ointment-like drug composition (B), this pod preferably comprising a layer (A) of a laminate of poly(ethylene terephthalate) film (PET) and an ethylene vinyl acetate film (EVA) joined by a rupturable heat seal at its periphery to a layer (C) comprising a laminate of PET film and a film of low density polyethylene (PE); in accordance with techniques well known in the art, pod (A) (C) is so constructed that it will contain ointment (B) until it has been subjected to a pod rupturing force, at which time the pod is ruptured and the ointment released to contact spreading layer (E) (or barrier layer (F) if the optional layer (E) is omitted) as described below;

(iii) an ointment-like drug-containing composition (B) comprising (1) about 5-10 wt. % of an antianginal nitrate, preferably TNG, (2) an inert carrier for the nitrate (when the nitrate is TNG the carrier is preferably lactose or silica gel which is preferably present in a ratio of from about 9:1 to about 4:1 by weight, based on the weight of the TNG), (3) up to about 75 wt. % of an activator liquid comprising one or more chemicals for enhancing penetration of the TNG through barrier layer (F) and then through the skin, the activator liquid preferably being selected from isopropanol; isopropyl myristate; glycerine; di-n-butyl sebacate; aliphatic esters having about 3-20 total carbons, e.g. ethyl nonanoate; water; mineral oil; mixed esters of aliphatic acids and aromatic alcohols (and vice versa) e.g. phthalic acid esters, and diethylene glycol dibenzoate;

(iv) optionally, a spreading layer (E) comprising a woven or non-woven fabric, preferably polypropylene, which also acts as a support or intermediate layer connecting layers (D) and (F). (Conveniently, these layers may be heat sealed to each other.);

(v) a barrier polymer film (F) that is inherently resistant to the passage of the nitrate therethrough but becomes permeable to the nitrate by action of the activator(s) in ointment (B). [In a presently preferred embodiment, the barrier film is selected from (1) block copolymers of styrene and isoprene, and block copolymers of styrene and butadiene, e.g. Stereon 881A (Firestone); (2) block copolymers of ethylene/styrene/and butylene, e.g. Kraton (Shell Chemical Co.); (3) polyisobutylene rubber; (4) poly(vinyl isobutyl ether); (5) vinyl polymers such as poly(hexene-co-propylene); (6) poly(vinyl acetate) and copolymers of vinyl acetate with ethylene or with vinyl chloride; and (7) cellulose acetate butyrate.];

(vi) a non-irritating pressure-sensitive skin adhesive layer (G) that is freely permeable to the nitrate, e.g. poly(hexene-co-propylene) adhesives, adhesives containing EVA resin, polyurethane adhesives, silicone adhesives and acrylate adhesives;

(vii) a release liner (H), e.g. silicone-coated plastic film or paper.

Other known dosage forms can be adapted for administering nitrate to angina patients in accordance with the invention. Such dosage forms may include, pills, tablets, capsules and caplets for oral administrations, buccal tablets, topical creams and ointments, nasal sprays and inhalation devices, suppositories, implantable devices, etc.

In accordance with the present invention, the unit dosage of nitrate is preferably a daily dosage amount adequate to provide the necessary protection or relief from angina symptoms to the patient. The absolute amount provided will vary with the patient, the particular nitrate employed, and the dosage form to be administered. Also, the foregoing parameters will affect the delivery rates or fluxes employed in the several stages of drug delivery.

For example, when a transdermal nitroglycerine patch is employed, the total nitroglycerine delivered from a single patch (unit dosage) will be in the range of from about 1 to about 60 mg per day, preferably from about 2 to about 40 mg per day, more preferably from about 5 to about 30 mg per day for the typical patient. Transdermal nitroglycerine patches in accordance with the present invention will provide a washout period of from about 3 to about 12 hours, preferably from about 6 to about 9 hours, more preferably about 7 to about 8 hours for the typical patient. As employed herein, the term "washout period" will be understood to be a time interval during which the nitrate drug delivery to the patient's blood stream does not occur or occurs at such a low level as to be ineffective to cause tolerance to the drug in the patient. Preferably, the concentration of the drug in the blood serum is sufficiently low over a sufficient time interval to allow the disapperance of any tolerance effect that might have been caused by previous presence of the drug in the blood stream at a therapeutically effective level. The washout period is followed by an initial drug delivery period of up to about 5 hours, preferably from about 0.5 to about 4 hours, during which the delivery rate increases to an initial effective delivery flux (i.e. rate of drug delivery per unit area of transdermal device through the skin and into the vasculature) of from about $0.2 \times 10^{-8}$ to about $5 \times 10^{-8}$ g cm$^{-2}$ sec$^{-1}$, preferably from about $0.5 \times 10^{-8}$ to about $2 \times 10^{-8}$ g cm$^{-2}$ sec$^{-1}$, this initial effective delivery rate being achieved at from about 30 to about 120 minutes before the patient's expected awakening time, preferably from about 45 to about 90 minutes before such awakening time.

In this connection, in accordance with the practice of the present invention, the patch will be applied shortly before the patient's bedtime, the application time being selected in accordance with the foregoing parameters to achieve the foregoing timing. In general, this will be accomplished by removing the previous patch and applying the new patch at a convenient time before bedtime selected in consultation between the physician and the patient. For most people, the usual time for removing the old patch and applying a new one will be between about 9 p.m. and 12 p.m. local time.

The patches of the present invention are so designed that, contrary to currently available transdermal nitroglycerine patches, which provide substantially uniform delivery rates, patches in accordance with the present invention provide an increasing delivery rate (flux), this rate increasing to a final delivery rate of from about 125% to about 1,000% of the initial effective delivery rate, preferably from about 125% to about 600% thereof, more preferably from about 150% to about 400% thereof, over a ramp up delivery period of from about 8 to about 21 hours. The final delivery rate may be achieved at some point before the end of the ramp-up delivery period and this rate maintained substantially constant thereafter until the end of such period, or the delivery rate may continue to increase throughout the ramp-up period, in which event the final delivery rate is achieved at the end of the ramp-up period. In accordance with a presently preferred embodiment of the invention, the ramp up period (as well as drug delivery) is terminated by removing the patch from the patient's skin. As indicated above, this is accomplished at a preselected time before bedtime and is followed substantially immediately, or at least within about an hour or two, by application of a new transdermal patch in accordance with the invention.

In accordance with another embodiment of the invention, the treatment is accomplished by an oral delivery system, the particular dosage form being selected from capsules, caplets, tablets and similar pharmaceutically acceptable oral dosage forms. When an oral dosage form is employed, the unit dose will be selected to deliver to the patient from about 2.5 to about 50 mg. per day of nitroglycerine, preferably from about 5 to about 25 mg. per day. If isosorbide dinitrate or isosorbide 5-mononitrate is used as the nitrate, then the unit dosage will be from about 5 to about 300 mg. per day, preferably from about 25 to about 100 mg. per day. When the organic nitrate is pentaerythritol tetranitrate, the unit dosage will be from about 10 to about 200 mg/day, preferably from about 40 to about 160 mg/day. For erythrityl tetranitrate or isosorbide 2-mononitrate, the unit dosage will be from about 5 to about 100 mg/day, preferably from about 20 to about 50 mg/day.

Preferably, the entire daily unit dosage will be provided in one or two sustained release capsules, caplets or tablets designed to provide the desired drug delivery profile as described herein. Alternatively, combinations of different oral delivery dosage forms and strengths may be employed to achieve the desired drug delivery profile.

The following examples are presented to illustrate the practice of the present invention.

EXAMPLE 1

A simulated transdermal drug delivery device for the delivery of TNG was prepared on an extraction cell as follows:

A piece of woven polyester reinforcing fabric approximately 4.8 mils (0.12 mm) thick was hand coated with a solution containing 30 weight percent of poly (vinyl chloride-co-vinyl acetate) (PVC/VAc) (weight ratio 87/13 VC/VAc) and 7.5 weight percent of the plasticizer, di-2-ethylhexyl phthalate (DEHP), and dried to form a 7 mil (0.18 mm) thick plasticized polymer layer imbibed into and onto the polyester fabric at a coverage of about 11 mg cm$^{-2}$ containing 20 weight percent plasticizer and 80 weight percent polymer.

A second piece of woven polyester fabric as used above was hand coated as above with a 12 weight percent solution of poly(vinyl isobutyl ether) (PVIBE) in 2-butanone and dried to form a 6 mils (0.15 mm) thick layer of PVIBE imbibed into and onto the polyester fabric. This coating was employed as a barrier layer which is essentially impermeable to trinitroglycerine (TNG) in the absence of an activating agent such as n-1-octanol, but becomes very TNG permeable after the activating agent invades this layer. In these examples, the activating agent is contained in the drug delivery composition to be described hereafter.

Note: the use of the polyester reinforcing fabric in the preparations of the above two coatings was for experimental convenience in the casting, manipulation and lamination of flexible, and in the case of PVIBE, somewhat sticky, films. Such use can be obviated in commerically manufactured patches.

Next, the above two coatings were mounted as a laminate, along with nude mouse skin (to simulate the skin to be penetrated) and a very TNG permeable sheet of Silastic 500-1 plastic sold by Dow Corning (to reduce the removal of water-soluble extractables in the dermal layer of nude mouse skin), on the top of an extraction cell in the configuration shown below, with the Silastic 500-1 sheet in contact with the water in the cell:

The above construction was allowed to stabilize on the cell for two to three hours to form a baseline from which to begin the experiment. A drug delivery composition was prepared as an ointment containing 8 weight percent TNG, 32 weight percent silica gel (Silica Woelm 32-63 sold by Woelm Pharma. GMBH) and 60 weight percent n-1-octanol. The n-1-octanol in the ointment acts as an activating agent to render the barrier layer permeable to TNG as the n-1-octanol penetrates this layer.

Figure 2:
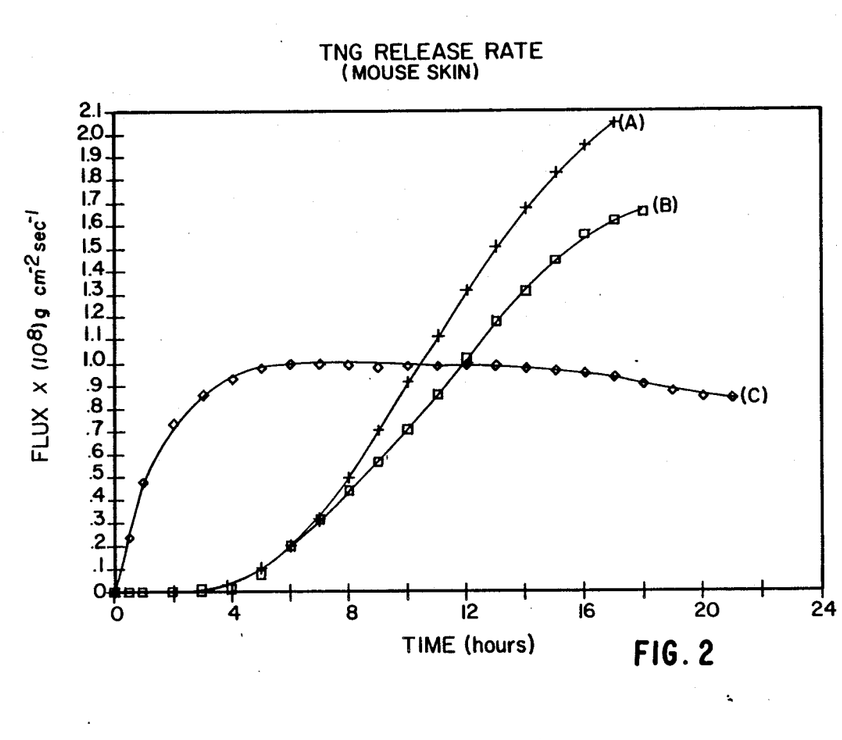
FIG. 2 is a graph of flux versus time for the experimental patches of Example 1.

At time $T_o$, the beginning of the experiment, the drug delivery ointment was poured or extruded onto the plasticized PVC/VAc layer to form the drug delivery layer at a TNG coverage of 15 mg cm$^{-2}$. The extraction fluid in the cells (here, distilled water at 37° C.) was continuously stirred and replenished. The effluent from the extraction cell was continuously monitored for TNG concentration with a UV detector set at 218 nm. In the graph of FIG. 2, the extraction rates are plotted as fluxes, i.e., area normalized rates vs time, for up to 24 hours from time $T_o$ when the drug delivery composition was applied. The fluxes are reported as g cm$^{-2}$ sec.$^{-1}$ The nude mouse skins were the dorsal skins from nude mice of 5–6 weeks of age.

Plots A and B of flux vs time given in FIG. 2 are for two identical experiments run sequentially in the same extraction cell. As a control, a commercial transdermal TNG delivery patch, Ciba Transderm Nitro 10, sold by Ciba-Geigy Corp., was mounted in the extraction cell and tested the same way. Plot C shows flux vs time for this control.

Comparing the plots for the two experimental patches of Example 1 in FIG. 2 with that of the control, it is seen that (a) for the experimental patches there was negligible TNG flux for up to four hours, whereas the control showed no significant delay before delivery; (b) the fluxes of the experimental patches began to rise after four hours and reached approximately half the flux of the control after eight hours; (c) as their fluxes continued to rise, they reached about the same flux as the control after about 11 hours; and (d) the flux of the experimental patches reached about 1.6 times that of the control after about 16 hours. Thus, the time-modulated fluxes of the experiments provided a period of time during which no drug was being administered followed by a steadily increasing flux for at least the next 12 hours. By contrast, the control, after a rapid increasing delivery rate over the first few hours, levelled off to a substantially steady delivery rate at about the fifth hour, and started to show a slightly decreasing delivery rate after about the thirteenth hour.

Figure 3:
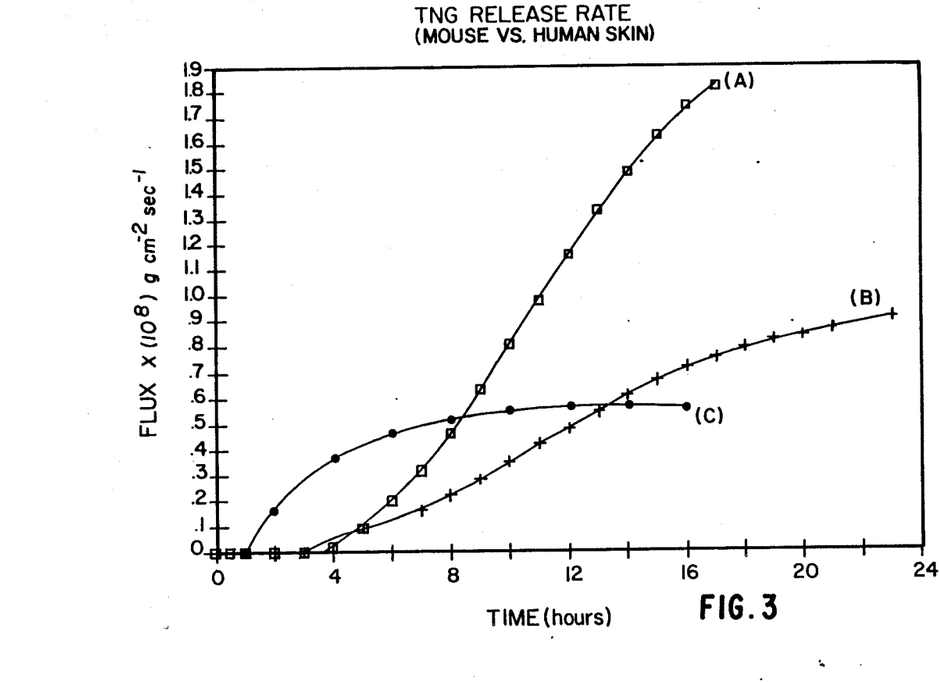
FIG. 3 is a graph of flux versus time for the experimental patches of Example 2, comparing flux rate in vitro through human skin and mouse skin.

FIG. 3 compares the flux (J) vs. time data from in vitro extraction experiments through mouse and human skin. The uppermost curve (A) shows the average of the two experimental runs depicted in FIG. 2 on nude mouse skin whereas curve B, which begins to rise after a delay of three hours, shows the flux vs time for an identical device on human abdominal (lipectomy) skin. Also shown in FIG. 3 are the flux data (curve C) for the control (Ciba Transderm 10) (i.e., constant delivery rate) device on human abdominal (cadaver) skin. Whether on nude mouse skin or on human skin the device of this invention did not begin delivering drug until three hours after patch application. The control patch, however, began delivering drug through the specimen just one hour after patch application. Furthermore, on human skin, the flux from the control device rose rapidly whereas that from the device of this invention, after the three hour delay, rose much more slowly, but continued to rise throughout the extraction, exceeding that from the control device after thirteen hours. The time modulation of flux with the device from this invention was, therefore, pronounced while that from the control device was at most modest.

EXAMPLE 2

Two laminates were prepared and mounted for testing in extraction cells as described for Example 1 except that the poly(vinyl isobutyl ether) barrier layer was omitted, and the drug delivery compositions employed in the experiments had the following compositions in weight percent and TNG coating coverages:

|  | Example 2A | Example 2B |
|---|---|---|
| Di-n-butyl sebacate (DBS) | 5 (wt. %) | 15 (wt. %) |
| n-1-Decanol | 45 | 35 |
| Lactose | 45 | 45 |
| TNG | 5 | 5 |
| Total | 100 | 100 |
| TNG Coverage (mg/cm$^2$) | 14 | 12 |

DBS is a plasticizer for vinyl chloride rich polymers. DEHP, used in Examples 1–3, is also a plasticizer for polymers of vinyl chloride and copolymers rich in vinyl chloride. Well plasticized vinyl chloride-rich polymers are permeable to n-1-decanol and TNG.

Figure 4:
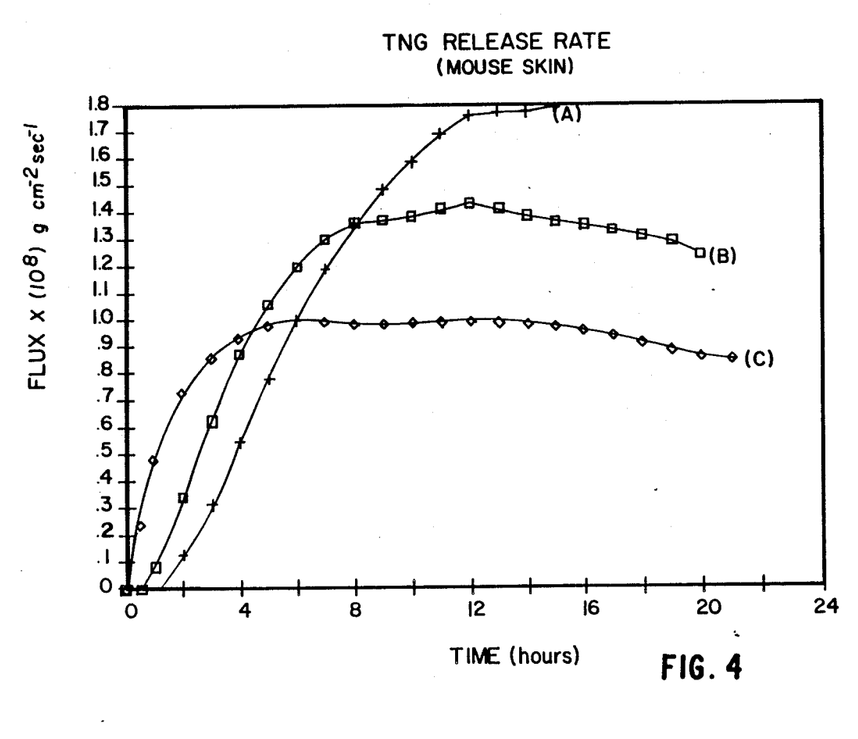
FIG. 4 is a graph of flux versus time through mouse skin for the experimental patches of Example 2 as well as the control for Examples 1 and 2.

FIG. 4 illustrates how the delay and subsequent increase in flux can be varied by changing the relative amounts of the activating agents (here DBS and 1-decanol) in the drug delivery composition. Clearly, increased n-1-decanol level (45%) with commensurately decreased DBS level (5%) (curve A) helped to extend the delay in the near term and led to a greater TNG flux in the longer term vs curve B (15% DBS; 35% n-1-decanol).

In comparing the experimental devices of Example 2 with a control designed to provide constant flux, here the commercially available patch, Ciba Transderm Nitro 10, (curve C) one sees that the TNG flux from the former lagged that from the latter for the first four to six hours of the extraction, after which the TNG flux from the patch of Example 2 continued to rise while the TNG flux from the control patch remained virtually constant. In other words the patches of this invention, due to the action of the barrier layers and the nature of the activating agents in the drug delivery composition, achieved significant modulation of drug delivery with time, whereas the control delivered an almost constant flux of drug while on the skin.

The barrier layers employed in Examples 1 and 2 delay TNG delivery as a function of the time required for TNG to diffuse through the cross-section of these layers. This delay can be extended by choosing as a part of the cross-section at least one elastomeric polymer film that is almost impermeable to TNG in the absence of an activating agent, but is rendered highly permeable to TNG in the presence of an activating agent. Note that in a commercial device, the drug delivery composition would be isolated from the barrier layer(s) until the device is to be applied for use. For example, the drug delivery composition can be contained in an impermeable pod that is burst upon application of the device to the skin so as to extrude the composition uniformly across the adjacent layer, which may be a preliminary spreading layer or the barrier layer, in position to penetrate that adjacent layer and the remaining layers of the element. Note also that the activating agent could be contained in a composition or compartment separate from the drug delivery composition, but should, in any event, be compatible therewith.

EXAMPLE 3

A transdermal drug delivery device was prepared as follows:

A coating solution of 20% Kraton G1652, a block terpolymer of styrene, ethylene, and butylene, in toluene was hand-coated on a silicone-coated poly(ethylene terephthalate) (PET) release liner sold by Johnson Laminating and Packaging, Inc., and dried to form a barrier layer about 18 mils (0.46 mm) thick.

A coating solution of about 15% poly(hexene-co-propylene) hot-melt, pressure-sensitive adhesive sold by Texas Eastman Co. in toluene was hand-coated onto a silicon-coated PET release liner as described above and dried to form a pressure-sensitive adhesive layer about 1.5 mils (0.04 mm) thick.

The Kraton G1652 barrier layer prepared above was laminated to a sheet of nonwoven polypropylene (PP) fabric [Cycleon sold by Kimberly-Clark Co., about 1.5 oz/yd$^2$ (51 g/m$^2$)] by placing the Kraton G1652 layer against the polypropylene and heating at about 250° F. (121° C.) for about two sec in a heat-sealing device. The release liner was then removed from the other side of the Kraton G1652 layer and the Cycleon non-woven fabric-supported Kraton G1652 layer was then laminated to the poly(hexene-co-propylene) pressure-sensitive adhesive layer prepared above with firm pressure to produce the following structure:

| |
|---|
| Nonwoven polypropylene |
| Kraton G1652 Barrier Layer |
| Pressure-Sensitive Adhesive |
| Release Liner |

Next, a pouch for the drug composition was prepared by heat-sealing on three edges a rectangular piece of a PET/poly(ethylene-co-vinyl acetate) (EVA) laminate sold by 3M under the trademark "Scotchpack Brand Heat Sealable Polyester Film #113" to a second rectangular piece of a PET/low density polyethylene (PE) laminate, sold by 3M under the trade name "Scotchpack Brand Heat Sealable Polyester Film 132", at about 275° F. (135° C.) for 0.5 sec. These materials were selected to make the drug-containing pods because they can be heat sealed under a wide range of conditions to produce a wide range of seal strengths. The pouch was filled through the open side with about 200 μL of the trinitroglycerine (TNG) drug composition described below, and the open side was also sealed as above to form an enclosed pouch filled with the TNG drug composition to be delivered.

The drug composition placed in the pouch was prepared by mixing 16.1 parts of isopropyl alcohol (IPA), which serves as an activator for the Kraton G1652 barrier layer, and 30.0 parts of mineral oil, with 17.5 parts of SDM-17, a TNG composition sold by ICI Americas containing 10% TNG in 90% lactose as a carrier.

The four-layer element containing the Kraton G1652 barrier layer was heated in a ring around the perimeter at 350° F. (177° C.) for one second to fuse the fibers of the nonwoven fabric into a small annular ring of a solid, impermeable mass in the ring area around the perimeter of the element. This fused ring provides a platform for receiving the pod of drug and making the final seal. The pouch containing the drug composition was placed in the ring adjacent to the Kraton G1652 layer and covered with a sheet of a poly(ethylene terephthalate) (PET)/polypropylene (PP) laminate sold under the tradename "Scotchpack Brand Heat Sealable Polyester Film #126" by 3M Company and heat sealed to the previously fused annular ring for one second at 350° F. (177° C.) to form an occlusive backing layer to complete the preparation of the transdermal drug delivery element. This final "fusion seal" of the backing layer to the laminate is very strong. The final element had the structure shown in FIG. 1.

In use, the element is, in a presently preferred embodiment, first activated by squeezing and massaging the pouch containing the drug composition to burst the pouch and spread the drug composition onto the adjacent spreading layer or barrier layer. Next, the release liner is removed by stripping away from the device, and the element is laminated by hand to the skin of the patient to be treated.

In order to facilitate testing to evaluate the components critical to the control of the delivery rate profile, another element was prepared as described above except that the pod, drug composition, occlusive backing layer, and non-woven polypropylene layer were omitted.

The element was tested by removing the release liner and laminating the element to a layer of human stratum corneum and mounting the laminate in a Franz cell. The drug delivery element formed the donor side of the cell and the receiver side of the cell contained continuously-stirred, phosphate-buffered saline solution. The test was initiated by pouring a sample of 420 mg of the drug composition prepared as described in the first part of this example onto the barrier layer. An aliquot of the receiver solution in the cell was removed and replaced with an equal volume of fresh saline solution after the 1st, 2nd, 4th, 6th, 8th, and 24th hours. The flux at each time period was calculated from the concentration of TNG in each sample determined by high performance liquid chromatography (HPLC) analysis. The "delay" time, reported to represent the time period from activation until drug delivery, is defined as the time period during which the delivery flux is less than $0.14 \times 10^{-8}$ g/cm$^2$/sec.

Figure 5:
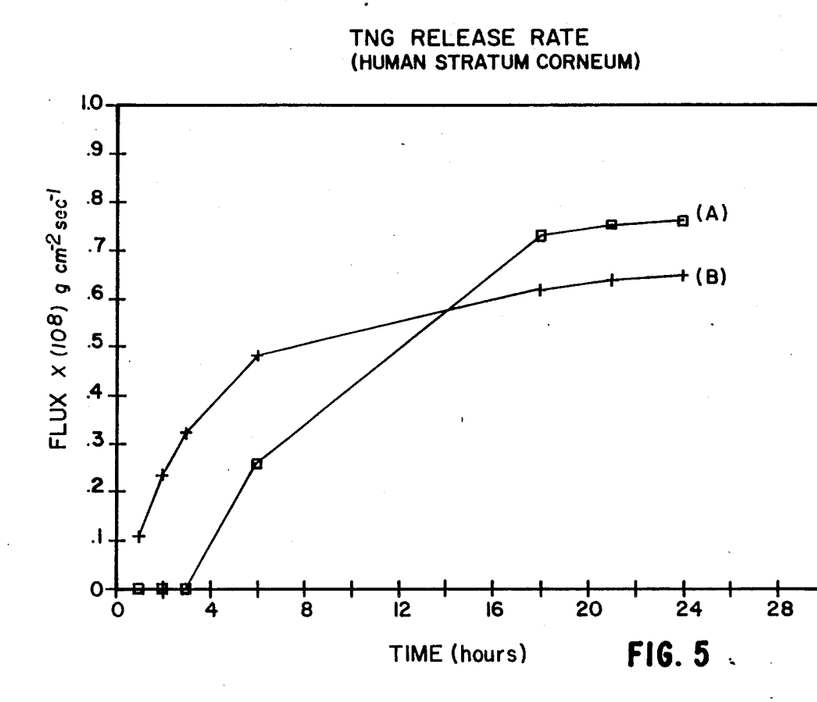
FIG. 5 is a graph of flux versus time for the experimental patch of Example 3 as well as for the control through human stratum corneum.

The delay was 4.6 hours and the fluxes after 8 and 24 hours were $0.33 \times 10^{-8}$ and $0.75 \times 10^{-8}$ g cm$^{-2}$ sec$^{-1}$, respectively. For the experimental element, the flux constantly increased from onset of delivery through the remainder of the 24 hour period. By contrast, a commercially purchased device, CIBA Transderm Nitro, used as a control showed essentially no delay and little continued flux increase after 6 hours. Thus, the flux rose quickly over the first 6 hours and then remained essentially at a steady state. These results are illustrated in FIG. 5, wherein curve A depicts the flux for the experimental element and curve B shows the flux for the control, both through human stratum corneum.

The invention has been described in detail with particular reference to preferred embodiments thereof, but it will be understood that variations and modifications can be effected within the spirit and scope of the invention.

What is claimed is:

1. A transdermal patch for delivering a organic nitrate drug to a patient comprising, in combination:
   (i) an occlusive backing layer;
   (ii) a rupturable pod reservoir for containing an ointment composition;
   (iii) an ointment drug-containing composition disposed within said pod; said composition comprising said drug, a carrier for said drug and an activator liquid activator selected from the group consisting of ethanol, propanol, isopropanol, isobutanol, hexanol, octanol, decanol, dodecanol, ethylene glycol, propylene glycol, 1,3-propanediol, glycerin, ethyl, acetate, isopropyl myristate, lauryl myristate, decyl propionate, bis(2-ethylhexyl) phthalate, bis-(2-ethylhexyl) sebacate, di-n-butyl sebacate, diisopropyl adipate, mineral oil, bis(n-octyl) phthalate, cetyl alcohol, dibutyl phthalate, diethyl sebacate, ethyl lactate, ethyl phthalate, glycerol monostearate, glycerol distearate, glycerol tristearate, isopropyl palmitate, isopropyl stearate, N,N-bis(2-hydroxyethyl)dodecanamide, lauric myristic monoethanolamide, lauryl lactate, myristyl alcohol, n-decyl methylsulfoxide, N,N-dimethylacetamide, oleyl alcohol, phenylethyl alcohol, sodium lauryl sulfate, sodium stearate, stearyl alcohol, wood alcohols, 1,2,6-hexanetriol, water, and 2-amino-2-methyl-1-propanol;
   (iv) a barrier polymer film that is inherently resistant to the passage of said drug therethrough but becomes permeable to said drug by action of said activator liquid in said drug composition; and
   (v) a non-irritating pressure-sensitive adhesive layer that is permeable to said drug.

2. Means for preventing tolerance to an organic nitrate drug during long term therapy involving repeated administration of said drug, said means comprising a plurality of the patches of claim 1.

3. The patch of claim 1 wherein said barrier polymer is selected from the group consisting of rubbery vinyl copolymers, copolymers of styrene with ethylene and butylene or with butadiene; styrene-butadiene and styrene-isoprene copolymers; polymers of vinyl ethers; polymers of vinyl chloride, polymers of vinyl acetate; acrylic and acrylamide polymers; homopolymers and copolymers of ethylene, propylene, isoprene and butadiene, and low molecular weight polyethers.

4. The patch of claim 1 wherein said barrier polymer is selected from the group consisting of block copolymers of styrene and isoprene, block copolymers of styrene and butadiene, block copolymers of ethylene/styrene/ and butylene, polyisobutylene rubber, poly(vinyl isobutyl ether), poly(hexene-co-propylene), poly(vinyl acetate), copolymers of vinyl acetate with ethylene or with vinyl chloride, and cellulose acetate butyrate.

5. The patch of claim 1 wherein said barrier polymer is selected from the group consisting of poly(vinyl chloride-co-vinyl acetate), styrene-isoprene copolymers, poly(vinyl acetate), poly(vinyl isobutyl ether), poly(ethylene glycol) and cellulose acetate butyrate.

6. The patch of claim 5 wherein said activator is selected from n-decanol, n-octanol, dibutyl sebacate, bis(2-ethylhexyl) phthalate, isopropanol, glycerol, 1,3-propanediol, diisobutyl adipate, benzyl butyl phthalate and water.

7. The patch of claim 5 wherein said barrier polymer is selected from poly(vinyl chloride-co-vinyl acetate) and styrene-isoprene copolymers.

8. The patch of claim 5 wherein said barrier polymer is selected from poly(vinyl acetate) and cellulose acetate butyrate.

9. The patch of claim 5 wherein said barrier polymer is poly(vinyl isobutyl ether).

10. The patch of claim 5 wherein said barrier polymer is poly(ethylene glycol).

11. The patch of claim 4 wherein said barrier polymer is an ethylene-styrene-butylene block copolymer.

12. The patch of claim 7 wherein said activator is selected from the group consisting of dibutyl sebacate, bis(2-ethylhexyl) phthalate and benzyl butyl phthalate.

13. The patch of claim 8 wherein said activator is selected from the group consisting of diisobutyl adipate and benzyl butyl phthalate.

14. The patch of claim 9 wherein said activator is selected from the group consisting of n-decanol and n-octanol.

15. The patch of claim 10 wherein said activator is selected from the group consisting of glycerol, 1,3-propanediol and water.

16. The patch of claim 12 wherein said barrier polymer is poly(vinyl chloride-co-vinyl acetate).

17. The patch of claim 3 wherein said barrier polymer is selected from the styrene-isoprene and the styrene-butadiene copolymers and said activator is selected from dibutyl sebacate and bis(2-ethylhexyl) phthalate.

18. The patch of claim 13 wherein said barrier polymer is poly(vinyl acetate).

19. The patch of claim 4 wherein said barrier polymer is cellulose acetate butyrate and said activator is diisobutyl adipate.

20. The patch of claim 1 which further comprises a release liner overlaying the adhesive layer.

21. The patch of claim 1 wherein said occlusive backing layer comprises a laminate of an occlusive polymeric film and a heat sealable film.

22. The patch of claim 21 wherein said occlusive polymeric film is a polyester film and said heat sealable film is a polyolefin film.

23. The patch of claim 1 wherein the walls of said rupturable pod are impermeable to said drug-containing composition disposed therewithin.

24. The patch of claim 1 wherein said nitrate drug comprises an organic nitrate selected from nitroglycerine, isosorbide dinitrate, isosorbide-2-mononitrate, isosorbide-5-mononitrate, pentaerythritol tetranitrate, and erythrityl tetranitrate.

25. The patch of claim 11 wherein said activator is selected from isopropanol, isopropyl myristate and N,N-bis(2-hydroxyethyl)dodecanamide.

26. The patch of claim 1 wherein said activator is a plastisizer for said barrier polymer film, and said barrier polymer film becomes more permeable to the drug as it is plasticized by contact with said activator in said drug-containing composition.

27. The transdermal patch of claim 1 wherein said means for bringing the patch into drug delivery relationship with the patient comprises an adhesive peripheral boundary on the patch for adhering the patch to the skin of the patient.

* * * * *